United States Patent [19]

Darsow et al.

[11] Patent Number: 5,750,803
[45] Date of Patent: May 12, 1998

[54] PROCESS FOR THE PREPARATION OF D,L-MENTHOL

[75] Inventors: Gerhard Darsow, Krefeld; Gerd-Michael Petruck, Erkrath, both of Germany

[73] Assignee: Bayer Aktiengesellschaft, Leverkusen, Germany

[21] Appl. No.: 644,783

[22] Filed: May 10, 1996

[30] Foreign Application Priority Data

May 17, 1995 [DE] Germany .................. 195 18 024.0

[51] Int. Cl.$^6$ .................. C07C 35/12; C07C 27/00
[52] U.S. Cl. .................. 568/830; 568/829
[58] Field of Search .................. 568/829, 830; 562/324, 325

[56] References Cited

U.S. PATENT DOCUMENTS 2,843,636  7/1958  Booth .
4,058,571  11/1977  Biedermann .
5,300,706  4/1994  Immel et al. .

OTHER PUBLICATIONS

Ullmanns Encyclopedia of Industrial Chemistry, 3rd Ed., vol. 17, pp. 24–25, (1996).
Chemical Abstracts, vol. 112, No. 1, Jan. 1, 1990, Columbus, Ohio, US; abstract No. 7725, Zubareva, et al.: "Stereoselective hydrogenation of a menthol–isomenthol mixture on heterogeneous nickel, nickel–cobalt, and cobalt catalysts".
XP002012681 & IZV. AKAD. NAUK. SSSR, SER. KHIM., Bd. 8, 1989, Seiten 1920–1923.

*Primary Examiner*—Gary Geist
*Assistant Examiner*—Karl J. Puttlitz, Jr.
*Attorney, Agent, or Firm*—Sprung Kramer Schaefer & Briscoe

[57] ABSTRACT

A continuous process is described for the preparation of D,L-menthol by catalytic hydrogenation of compounds which have the carbon skeleton of p-menthane containing at least one double bond and are 3-substituted by oxygen using hydrogen and/or by rearrangement of stereoisomers of menthol in the presence of hydrogen at temperatures of 150° to 230° C. and at pressures of 25 to 350 bar on fixed-bed catalysts made of support-free reduced shaped bodies made of pressed powders of cobalt (hydr)oxide, manganese (hydr)oxide, alkaline earth metal (hydr)oxides and, optionally, (hydr)oxides of elements of subgroup V and/or VI of the Periodic Table of the Elements.

9 Claims, No Drawings

PROCESS FOR THE PREPARATION OF D,L-MENTHOL

The invention relates to a process for the preparation of D,L-menthol from compounds which have the carbon skeleton of menthane containing at least one C=C double bond and are 3-substituted by oxygen, and/from stereoisomers of menthol in the presence of hydrogen and catalyst.

Among the naturally occurring cyclic terpene alcohols, L-menthol has a special position because of its cooling and refreshing action. L-Menthol is the main constituent of peppermint oil and is used in the perfume, flavouring and pharmaceutical industry.

Preparation of menthol by catalytic hydrogenation of compounds which have the carbon skeleton of menthane containing at least one C=C double bond and are 3-substituted by oxygen (for example thymol) leads to the D,L-racemate which can be resolved into optical antipodes. The 8 optically active menthols differ with respect to their organoleptic properties. L-Menthol has a characteristic peppermint odour and the refreshing action already mentioned; it is therefore the most valuable of the menthol stereoisomers. Attempts are therefore made to carry out hydrogenation is such a way that as much D,L-menthol (from which L-menthol can be obtained by resolution of the racemate) as possible is formed, or to rearrange as effectively as possible menthol stereoisomers, as arise, for example, in the hydrogenation of thymol.

German Auslegeschrift 2 314 813 and EP-A 563 611 disclose that aromatic or partially hydrogenated cyclic compounds which have the carbon skeleton of menthane containing at least one C=C double bond and are 3-substituted by oxygen can be hydrogenated with hydrogen and/or stereoisomers of menthol can be rearranged in the presence of hydrogen, a cobalt/manganese catalyst or a fixed-bed catalyst which contains palladium, ruthenium, rhodium or a mixture of these elements as active contituents, and alkali metal hydroxides and/or alkali metal sulphates as promoters, on a support doped with a rare earth metal and with manganese, being used.

U.S. Pat. No. 2,843,636 describes the isomerization of stereoisomers of menthol to give D,L-menthol using hydrogen in the presence of a copper chromite catalyst.

These prior art processes either produce too many by-products (which become of importance as interference by accumulation, in particular in the case of a continuous procedure), or the catalysts used lose their initial activity too rapidly, are of limited mechanical stability, may only be loaded to a limited extent and/or make reprocessing the used catalysts more difficult.

There was therefore the desire to provide high-loading capacity and long-lived catalysts for the preparation of D-menthol to D,L-menthol which are free from complicated support systems and are therefore to be reprocessed.

Surprisingly, the problem described may be solved using support-free fixed-bed catalysts, which can be obtained by reduction of shaped bodies made of pressed metal(hydr)oxide powders. The term "metal (hydr)oxides" in the context of this invention means metal oxides and/or metal hydroxides.

The invention therefore relates to a continuous process for the preparation of D,L-menthol by catalytic hydrogenation of compounds which have the carbon skeleton of menthane containing at least one C=C double bond and are 3-substituted by oxygen using hydrogen and/or by catalytic rearrangement of menthol stereoisomers in the presence of hydrogen, characterized in that support-free shaped bodies serving as catalysts are used, which are obtainable by reduction of shaped bodies made of pressed powders of cobalt (hydro)oxide, manganese (hydr)oxide and alkaline earth metal (hydr)oxides with or without one or more (hydr)oxides of metals of subgroup V and/or VI of the Periodic Table of the Elements.

The starting compounds used for the process of the invention are known (Ullmanns Encyclopädie der technischen Chemie [Ullmanns Encyclopaedia of Industrial Chemistry], 3rd Edition, Munich, 1966, Vol. 17, pp. 24, 25; U.S. Pat. No. 2,843,636). Examples which may be mentioned are: thymol, menthone, methenone, D- and L-menthol, D- and L-neomenthol, D- and L-isomenthol, D,L-neomenthol, D,L-isomenthol. These compounds can be used either individually or in any desired mixtures.

For the catalysts to be used according to the invention, the contents (in each case calculated as metal) of Co are 40 to 65% by weight, of Mn are 10 to 20% by weight, the alkaline earth metal contents are 0.2 to 5% by weight and, if present, the contents of metals of subgroup V and/or VI of the Periodic Table of the Elements (Mendeleev) are in total up to 7% by weight, preferably 0.5 to 7% by weight, in particular 1.0 to 3.5% by weight, of the total (hydr)oxide powder. The remainder to 100% by weight is oxygen for the compounds present in oxidic form. Although a catalyst of this type can be used for the hydrogenation step of the invention without a content of (hydr)oxides of subgroup V and VI of the Periodic Table of the Elements, it preferably additionally contains at least one (hydr)oxide of metals of subgroup V and/or VI of the Periodic Table of the Elements. In the event of the use of a plurality of (hydr)oxides of elements of subgroup V and/or VI of the Periodic Table of the Elements, each of these (hydr)oxides is present in an amount which is not less than 20% and not more than 80% of the said total range of 0.5 to 7% by weight.

Alkaline earth elements which are suitable are, especially, magnesium, calcium, strontium and barium, preferably strontium and barium. Elements of subgroup V which are suitable are preferably vanadium, niobium and tantalum, and elements of subgroup VI, preferably, chromium, molybdenum and tungsten. The elements of subgroup V and VI acting as promoters can either be used individually or as a mixture of a plurality of these elements.

The support-free shaped bodies can be prepared by conventional methods by pressing the metal (hydr)oxide powder mixtures (optionally after heating in advance at higher temperatures), for example on tableting or pelleting machines, at high pressure, to improve the adhesiveness of the metal (hydr)oxide particles, graphite and/or adhesives being able to be used in amounts of 0.5 to 3% by weight, based on the total weight of the constituents to be pressed. Examples of shaped bodies are tablets, beads or granules having diameters of 3 to 7 mm. Tableted shaped bodies can further be provided with an axial bore hole to enlarge the external surface area. Shaped bodies of this type have a smooth surface, viewed macroscopically.

The pressed metal (hydr)oxide shaped bodies have a high compressive strength of 300 to 800N, preferably 400 to 600N/cm$^2$, on the planar shaped body surface and 50 to 200N, preferably 80 to 140N, on the curved shaped body surface. The internal surface area of the pressed metal (hydr)oxide powders is 30 to 200 m$^2$/g, preferably 80 to 160 m$^2$/g. The compressive strength of the support-free shaped bodies can be determined in accordance with DIN 50 106, and the internal surface area in accordance with F. M. Nelsen and F. T. Eggertsen, Analyt. Chem. 30 (1958), 1387–1392 or S. J. Gregg and S. W. Sing, Adsorption, Surface Area and Porosity, London 1982, chapters 2 and 6.

Before use, the shaped bodies made of pressed (hydr) oxide powders must be carefully reduced. This is preferably achieved by using a reduction gas which comprises an inert gas/hydrogen mixture in which the hydrogen content at the start is 10 to 15% by volume. The inert gas preferably used is nitrogen. The reduction proceeds, for example, in the course of a period of about 24 hours at a reduction temperature of 180° to 220° C., the proportion of nitrogen in the gas mixture being more and more decreased in the end phase of the reduction, until the gas mixture comprises solely hydrogen. The reduction is complete when hydrogen is no longer consumed and, as a result, the reaction water is no longer formed.

The reactors can be individual high-pressure tubes made of steel or a steel alloy which are wholly or partially filled with the shaped bodies, in which case, with relatively large tube cross-sections, employing the support-free shaped bodies on trays (for instance wire baskets or similar) can be useful; however, high-pressure tube bundles can also be used within a collective shell, the individual tubes again being wholly or partly filled with the support-free shaped bodies.

The process of the invention can be carried out in the gas phase or trickling phase with the catalysts arranged in the fixed bed, during the course of the process, at least 10 times the molar amount of hydrogen per mole of starting material passing through the reactor. A temperature of 150° to 230° C., preferably 160° to 210° C. and a pressure of 25 to 350 bar, preferably 100 to 300 bar, are employed.

The process of the invention can be carried out with or without solvent. Suitable solvents which are inert under the reaction conditions are, for example, methanol, ethanol and isopropanol.

The hourly catalyst loading can be between 400 and 1000 g of reaction mixture per liter of catalyst. In the context of the process according to the invention, very high catalyst service lives of 20,000 to 25,000 hours are to be achieved. These service lives are many times higher than are described in earlier publications (e.g. German Auslegeschrift 2 314 813).

The hydrogenations, racemizations and isomerizations proceeding in the process of the invention surprisingly scarcely lead to the formation of unutilizable by-products, such as undesirable hydrocarbons.

The reaction mixture obtained contains sufficient D,L-menthon that it can be worked up to this desired product by simple distillation. Using the process of the invention, not only are excellent results obtained in the hydrogenation of thymol, but excellent yields in the conversion of the other starting compounds mentioned above are also obtained.

After the separation by distillation of the desired D,L-menthol, the distillation first runnings together with distillation bottom product, with addition of fresh starting product, for example with addition of 10 to 80% by weight of thymol, based on this distillation residue, can be returned to the reaction. The amount of starting material corresponding to the D,L-menthol taken off by distillation is replaced. The hydrogen not consumed in the process of the invention can be recirculated.

The D,L-menthol produced, after removal of the distillation first runnings and the distillation bottom product, is obtained in a purity of $\geq 99.9\%$ by weight and is therefore usable without further purification in all further processing.

The colourless and glass-clear product obtained after the distillation has a melting point of 41° C. and can be crystallized in crystallization equipment of conventional type.

In the examples below, the symbol $m^3$ (S.T.P.) denotes cubic meters after conversion to standard conditions (1 bar, 25° C.).

EXAMPLES

Example 1

A vertically upright, thermally insulated high-pressure tube made of stainless acid-resistant steel of 45 mm in internal diameter and 1 m in length which had been flushed oxygen-free in advance with nitrogen was packed with 1.4 l of shaped bodies produced by tableting powders of cobalt (hydr)oxide, manganese (hydr)oxide, barium (hydr)oxide and vanadium (hydr)oxide. The cobalt content of the tablets was 53% by weight, the manganese content was 14% by weight, the barium content was 1.1% by weight and the vanadium content was 1.2% by weight. The tablets, at a cylinder height of 5 mm and a diameter of 5 mm, had a compressive strength of $420 N/cm^2$ on the planar cylinder surface and 125N on the curved shaped body surface and an internal surface area of 168 $m^2/g$.

The tablets were first dried for 6 hours in a nitrogen stream (temperature: max. 200° C., flow rate 5 $m^3$ (S.T.P.) of $N_2$/h. The activation was performed under a nitrogen pressure of 200 bar at a temperature between 180° and 220° C., in which case hydrogen was gradually admixed to the nitrogen, the proportion of nitrogen admixed initially being 10 to 15% by volume. In the course of 24 hours, the proportion of nitrogen in the gas mixture was decreased more and more until finally pure hydrogen flowed through the reactor. The activation was ended as soon as reaction water no longer collected in the downstream separator.

After the catalyst had been activated, the hydrogen pressure in the reactor system was increased to 300 bar. 700 g of thymol (purity: 99.9% by weight) together with 15 $m^3$ (S.T.P.) of hydrogen were then pumped per hour from top to bottom through the high-pressure tube at a pressure of 300 bar, the thymol having been heated to a temperature of 170° C. prior to entry into the high-pressure tube in an upstream electrically heated heat exchanger.

The reaction product leaving the reaction tube was cooled to a temperature <60° C. in a second heat exchanger (water cooler) at 300 bar hydrogen pressure and separated in a gas separator from excess hydrogen, which was recycled to the reaction system.

The thymol throughput corresponded to a catalyst loading of 0.5 kg/l of catalyst×h. The catalyst was still highly active even after a running time of 7400 h.

No thymol was found in the hydrogenation product.

After removal of the low-boilers and high-boilers by distillation, the D,L-menthol produced was obtained in a purity of 99.9% by weight.

Example 2

A high-pressure tube as in Example 1 was packed under inert gas with 1.4 l of shaped bodies produced by tableting powders of cobalt (hydr)oxide, manganese (hydr)oxide, barium (hydr)oxide, vanadium (hydr)oxide and tungsten (hydr)oxide. The cobalt content of the tablets was 47% by weight, the manganese content was 15% by weight, the barium content was 1.0% by weight, the vanadium content 0.8% by weight and the tungsten content was 0.6% by weight. The tablets, at a cylinder height of 5 mm and a diameter of 5 mm, had a compressive strength of $545 N/cm^2$ on the planar cylinder surface and 110N on the curved shaped body surface and an internal surface area of 117 $m^2/g$.

After activating this pressed metal (hydr)oxide powder mixture as in Example 1, the hydrogen pressure was increased to 300 bar.

560 g of thymol (purity: 99.9% by weight) together with 10 m$^3$ (S.T.P.) of hydrogen at a pressure of 300 bar were then continuously pumped per hour from top to bottom through the high-pressure tube, the thymol having been heated to a temperature of 175° C. prior to entry into the high-pressure tube.

The thymol throughput corresponded to a catalyst loading of 0.4 kg/l of catalyst×h. The catalyst was still highly active even after a running time of 6000 h.

No thymol was found in the hydrogenation product.

Example 3

A high-pressure tube as in Example 1 was packed under inert gas with 1.4 l of shaped bodies produced by tableting powders of cobalt (hydr)oxide, manganese (hydr)oxide, barium (hydr)oxide and molybdenum (hydr)oxide. The cobalt content of the tablets was 60% by weight, the manganese content was 18% by weight, the barium content was 1.5% by weight and the molybdenum content was 1.0% by weight. The tablets, at a cylinder height of 5 mm and a diameter of 5 mm, had a compressive strength of 736N/cm$^2$ on the planar cylinder surface and 105N on the curved cylinder surface and an internal surface area of 148 m$^2$/g.

After activation of this pressed metal (hydr)oxide powder mixture as in Example 1, the hydrogen pressure was left at 200 bar.

840 g of a mixture of menthol isomers comprising 75% by weight of D,L-neomenthol, 22% by weight of D,L-isomenthol and 3% by weight of D,L-neoisomenthol, together with 15 m$^3$ (S.T.P.) hydrogen at a pressure of 200 bar were then continuously pumped per hour from top to bottom of the high-pressure tube, the mixture of isomers and the hydrogen having been heated to 165° C. prior to entry into the high-pressure tube.

The throughput of the mixture of isomers corresponded to a catalyst loading of 0.6 kg/l of catalyst×h. The catalyst was still highly active even after a running time of 7600 h.

Example 4

A high-pressure tube as in Example 1 was packed under inert gas with 1.4 l of shaped bodies produced by tableting powders of cobalt (hydr)oxide, manganese (hydr)oxide, strontium (hydr)oxide and chromium (hydr)oxide. The cobalt content of the tablets was 53% by weight, the manganese content was 16% by weight, the strontium content was 0.9% by weight and the chromium content was 1.4% by weight. The tablets, at a cylinder height of 5 mm and a diameter of 5 mm, had a compressive strength of 594N/cm$^2$ on the planar cylinder surface and 125N on the curved cylinder surface and an internal surface area of 154 m$^2$/g.

After activating the catalyst as in Example 1, the hydrogen pressure was increased to 250 bar.

840 g of a thymol/menthol isomer mixture comprising 60% by weight of thymol, 25% by weight of neomenthol and 15% by weight of isomenthol, together with 15 m$^3$ (S.T.P.) of hydrogen at a pressure of 250 bar were continuously pumped per hour from top to bottom through the high-pressure tube, the reaction mixture having been heated to a temperature of 180° C. prior to entry into the high-pressure tube.

The product leaving the reaction tube was cooled to a temperature <60° C. and separated in a gas separator from excess hydrogen which was recycled to the reaction system.

The throughput of the reaction mixture corresponded to a catalyst loading of 0.6 kg/l of catalyst×h. The catalyst was still highly active even after a running time of 1900 h.

No thymol was found in the hydrogenation product.

Example 5

A high-pressure tube as in Example 1 was packed under inert gas with 1.4 l of shaped bodies produced by tableting powders of cobalt (hydr)oxide, manganese (hydr)oxide, barium (hydr)oxide and molybdenum (hydr)oxide. The cobalt content of the tablets was 53% by weight, the manganese content was 14% by weight, the barium content was 1.5% by weight and the molybdenum content was 1.1% by weight. The tablets, at a cylinder height of 5 mm and a diameter of 5 mm, had a compressive strength of 760N/cm$^2$ on the planar cylinder surface and 125N on the curved cylinder surface and an internal surface area of 149 m$^2$/g.

After activating the catalyst as in Example 1, the hydrogen pressure was increased to 300 bar.

700 g of a thymol/menthol isomer mixture were then continuously pumped per hour at a pressure of 300 bar from top to bottom through the high-pressure tube, the starting product having been heated to a temperature of 175° C. prior to entry into the high-pressure tube.

The thymol/menthol isomer mixture was made up of 60% by weight of thymol and 40% by weight of a menthol isomer mixture, as arises in the purifying distillation of the D,L-menthol produced according to Example 1 by combining the low-boilers and high-boilers of this distillation and was subsequently obtained by work-up by distillation of the reaction product arising in Example 5. The reaction mixture throughput corresponded to a catalyst loading of 0.5 kg/l of catalyst×h. The catalyst was still highly active even after a running time of 3000 h.

No thymol was found in the hydrogenation product.

After removal of the low-boilers and high-boilers by distillation, the D,L-menthol produced was obtained in a purity of 99.9% by weight.

No interfering minor components accumulated in the distillation first runnings and last runnings recycled to the reaction process, so that no first runnings or last runnings portions needed to be discarded.

We claim:

1. Continuous process for the preparation of D,L-menthol by catalytic hydrogenation of compounds which have the carbon skeleton of menthane containing at least one C=C double bond and are 3-substituted by oxygen using hydrogen and/or by catalytic rearrangement of menthol stereoisomers in the presence of hydrogen, characterized in that an unsupported shaped catalyst obtainable by reduction of shaped bodies made of pressed powders of cobalt (hydr) oxide, manganese (hydr)oxide and alkaline earth metal (hydr)oxides with or without one or more (hydr)oxides of metals of subgroup V and/or VI of the Periodic Table of the Elements is used.

2. Process according to claim 1, according to which the unsupported shaped catalyst made of pressed metal (hydr) oxide powders to be used for the reduction contains (each calculated as metal) 40 to 65% by weight of cobalt, 10 to 20% by weight of manganese, 0.2 to 5% by weight of alkaline earth metal and 0 to 7% by weight of metal of subgroup V and/or VI of the Periodic Table of the Elements, the percentages being based on the total amount of metal (hydr)oxide powder mixture and the remainder to 100% by weight being oxygen.

3. Process according to claim 1, characterized in that one or more (hydr)oxides of metals of group V and/or VI of the Periodic Table of the Elements (Mendeleev) are present in the pressed (hydr)oxide powder, whose total amount, calculated as metal, is 0.5 to 7% by weight of the total oxide powder.

4. Process according to claim 1, according to which the catalyst made of pressed metal (hydr)oxide powder has a compressive strength of 300 to 800 N/cm$^2$ on the planar shaped body surface and 50 to 200N on the curved shaped body surface (measured in accordance with DIN 50 106).

5. Process according to claim 1, according to which the catalyst made of pressed metal (hydr)oxide powder has an internal surface area of 30 to 200 m2/g.

6. Process according to claim 1, according to which the hydrogen pressure is 25 to 350 bar.

7. Process according to claim 1, according to which the rearrangement temperature is 150° to 230° C.

8. Process according to claim 1, characterized in that, during the process, at least 10 times the molar amount of hydrogen per mole of starting material passes through the reactor.

9. Process according to claim 1, characterized in that the D,L-menthol is removed by distillation from the reaction product of the hydrogenation of thymol or the rearrangement of the stereoisomers of menthol and the remaining reaction products, with addition of 10 to 80% by weight of thymol, based on the remaining reaction products, are returned to the reaction.

* * * * *